United States Patent
Aguilar et al.

(10) Patent No.: US 7,938,785 B2
(45) Date of Patent: May 10, 2011

(54) FUSION-BASED SPATIO-TEMPORAL FEATURE DETECTION FOR ROBUST CLASSIFICATION OF INSTANTANEOUS CHANGES IN PUPIL RESPONSE AS A CORRELATE OF COGNITIVE RESPONSE

(75) Inventors: Mario Aguilar, Cary, NC (US); Karen N Zachery, Raleigh, NC (US); Ming Qian, Cary, NC (US); Claudio Privitera, Albany, CA (US)

(73) Assignee: Teledyne Scientific & Imaging, LLC, Thousand Oaks, CA (US)

( * ) Notice: Subject to any disclaimer, the term of this patent is extended or adjusted under 35 U.S.C. 154(b) by 195 days.

(21) Appl. No.: 12/358,495

(22) Filed: Jan. 23, 2009

(65) Prior Publication Data

US 2009/0171240 A1 Jul. 2, 2009

Related U.S. Application Data

(63) Continuation-in-part of application No. 11/965,325, filed on Dec. 27, 2007.

(51) Int. Cl.
*A61B 13/00* (2006.01)
*A61B 5/103* (2006.01)
*A61B 5/117* (2006.01)
(52) U.S. Cl. ........................ 600/558; 600/587
(58) Field of Classification Search .................. 600/300, 600/544, 545, 546, 558, 587, 595; 702/127, 702/141–158
See application file for complete search history.

(56) References Cited

U.S. PATENT DOCUMENTS

| | | | |
|---|---|---|---|
| 5,617,872 A | 4/1997 | Scinto | |
| 5,632,282 A | 5/1997 | Hay | |
| 5,649,061 A | 7/1997 | Smyth | |
| 6,090,051 A | 7/2000 | Marshall | |
| 6,092,058 A | 7/2000 | Smyth | |
| 6,102,870 A | 8/2000 | Edwards | |
| 6,116,736 A * | 9/2000 | Stark et al. | 351/206 |
| 6,260,968 B1 * | 7/2001 | Stark et al. | 351/205 |
| 6,572,562 B2 | 6/2003 | Marshall | |
| 6,594,524 B2 * | 7/2003 | Esteller et al. | 607/45 |
| 6,820,979 B1 * | 11/2004 | Stark et al. | 351/206 |
| 7,146,218 B2 * | 12/2006 | Esteller et al. | 607/45 |
| 7,147,327 B2 * | 12/2006 | Stark et al. | 351/205 |
| 7,344,251 B2 | 3/2008 | Marshall | |
| 7,438,418 B2 | 10/2008 | Marshall | |
| 2002/0077534 A1 * | 6/2002 | DuRousseau | 600/300 |

(Continued)

OTHER PUBLICATIONS

Eric Granholm, Pupillometric measures of cognitive and emotional processes, International Journal of Psychophysiology 42 (2004) 1-6.

*Primary Examiner* — Jeffrey G Hoekstra
(74) *Attorney, Agent, or Firm* — Eric A. Gifford

(57) ABSTRACT

A computationally efficient and robust approach for monitoring the instantaneous pupil response as a correlate to significant cognitive response to relevant stimuli derives data samples d(n) of the pupil diameter (area), v(n) of pupil velocity and a(n) of pupil acceleration from the pupillary response and segments the data samples into a sequence of time-shifted windows. A feature extractor extracts a plurality of spatio-temporal pupil features from the data samples from the response and baseline periods in each window. A classifier trained to detect patterns of the extracted spatio-temporal pupil features for relevant stimuli generates an output indicative of the occurrence of absence of a significant cognitive response in the subject to a relevant stimulus.

16 Claims, 10 Drawing Sheets

U.S. PATENT DOCUMENTS

| | | |
|---|---|---|
| 2002/0099305 A1 | 7/2002 | Fukushima |
| 2004/0143170 A1* | 7/2004 | DuRousseau ................ 600/300 |
| 2004/0246441 A1* | 12/2004 | Stark et al. ................... 351/205 |
| 2005/0143629 A1* | 6/2005 | Farwell ........................ 600/300 |
| 2006/0181678 A1* | 8/2006 | Stark et al. ................... 351/206 |
| 2007/0038035 A1* | 2/2007 | Ehrlich et al. ............... 600/300 |
| 2008/0188777 A1 | 8/2008 | Bedziouk |

* cited by examiner

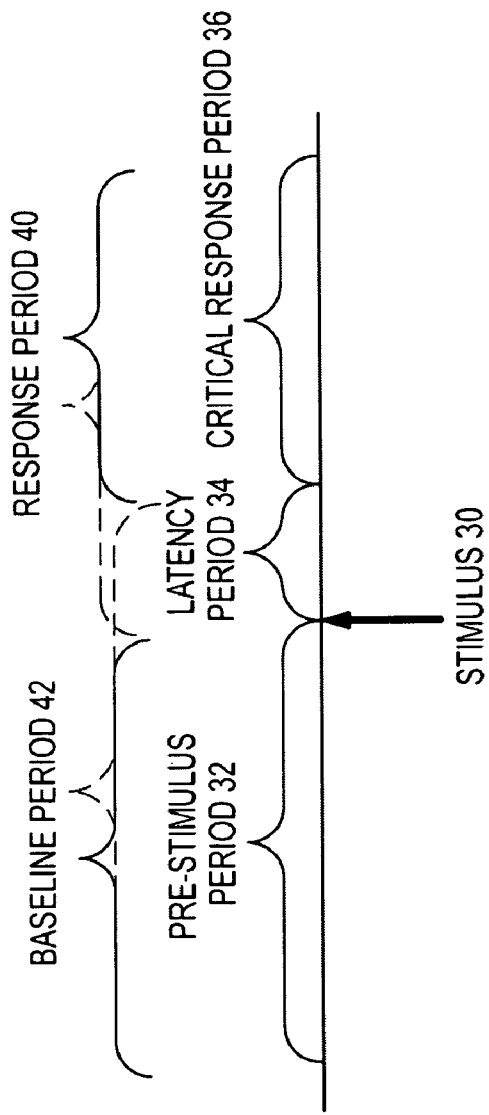
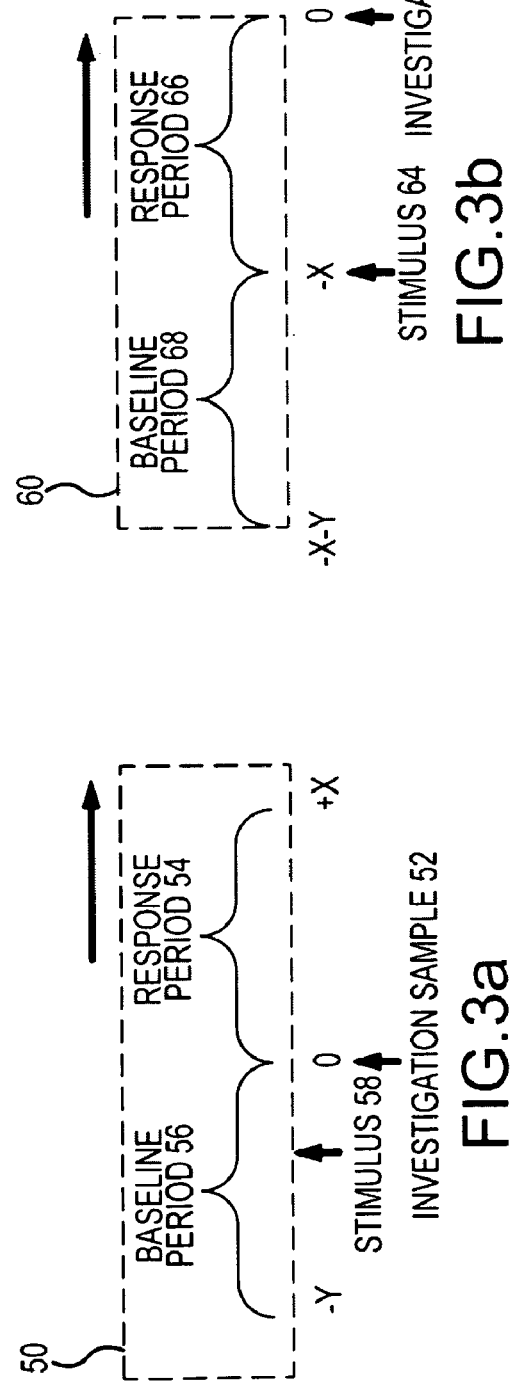

| FEATURE | DESCRIPTION |
|---|---|
| 1 | MAXIMUM ACCUMULATED DILATION VELOCITY OVER Tresponse |
| 2 | DIFFERENCE BETWEEN MAXIMUM ACCUMULATED DILATION VELOCITY OVER Tresponse AND Tbaseline |
| 3 | MAXIMUM DILATION VELOCITY OVER Tresponse |
| 4 | MAXIMUM DILATION ACCELERATION OVER Tresponse |
| 5 | DIFFERENCE BETWEEN MAXIMUM VELOCITY OVER Tresponse MINUS MEAN VELOCITY IN Tbaseline |
| 6 | DIFFERENCE BETWEEN MAXIMUM VELOCITY OVER Tresponse AND MAXIMUM VELOCITY OVER Tbaseline |
| 7 | DIFFERENCE BETWEEN MAXIMUM PUPIL AREA OVER Tresponse AND THE MEAN PUPIL AREA OVER Tbaseline |
| 8 | MAXIMUM PUPIL VELOCITY OVER Tresponse |
| 9 | PRODUCT OF FEATURES 7 (MEASURE OF AREA CHANGE) AND FEATURE 8 (MEASURE OF VELOCITY CHANGE) |
| 10 | MAXIMUM PUPIL DIAMETER OVER Tresponse |
| 11 | DIFFERENCE OF MAXIMUM DIAMETER OVER Tresponse MINUS MEAN DIAMETER OVER Tbaseline |
| 12 | ABSOLUTE DIFFERENCE BETWEEN MAXIMUM NORMALIZED DIAMETER OVER Tresponse AND THE MOVING AVERAGE OF PUPIL DIAMETER OVER Tbaseline |
| 13 | DIFFERENCE BETWEEN MAXIMUM NORMALIZED DIAMETER DEVIATIONS FROM MOVING AVERAGE OVER Tresponse AND Tbaseline |
| 14 | DIFFERENCE BETWEEN MAXIMUM NORMALIZED DIAMETER OVER Tresponse AND MOVING AVERAGE OVER Tbaseline |
| 15 | DIFFERENCE BETWEEN MAXIMUM NORMALIZED VELOCITY OVER Tresponse AND MOVING AVERAGE OVER Tbaseline |
| 16 | DIFFERENCE BETWEEN MAXIMUM NORMALIZED ABSOLUTE VELOCITY OVER THE LAST 4 SAMPLES IN Tresponse Tbaseline |
| 17 | DIFFERENCE BETWEEN MAXIMUM NORMALIZED VELOCITY OVER Tresponse AND Tbaseline |
| 18 | DIFFERENCE BETWEEN THE PERCENTAGE OF SAMPLES IN Tresponse AND Tbaseline ABOVE THE DIAMETER AT THE STIMULUS ONSET TIME (ASSUMED N SAMPLES PRIOR TO WINDOW CENTER) |
| 19 | DIFFERENCE BETWEEN THE PERCENTAGE OF SAMPLES IN Tresponse AND Tbaseline BELOW THE DIAMETER AT THE STIMULUS ONSET TIME (ASSUMED N SAMPLES PRIOR TO WINDOW CENTER) |
| 20 | AVERAGE ENERGY OVER Tresponse CALCULATED AS THE MEAN SQUARE VALUE FOR HISTOGRAM-BASED PROBABILITY DENSITY FUNCTION OF NORMALIZED DIAMETER |
| 21 | POWER RATIO OF THE PEAK SAMPLE IN A WINDOW CENTERED ON STIMULUS ONSET VERSUS ALL THE SAMPLES IN Tresponse AND Tbaseline |
| 22 | DIFFERENCE BETWEEN CONTOUR ENERGY IN THE PERIOD ENCOMPASSING Tresponse AND Tbaseline |

FIG.5a

| FEATURE | DESCRIPTION |
|---|---|
| 1 | MAXIMUM ACCUMULATED DILATION VELOCITY OVER THE LAST -X SAMPLES (T-x) |
| 2 | DIFFERENCE BETWEEN MAXIMUM ACCUMULATED DILATION VELOCITY OVER THE PREVIOUS -X SAMPLES (T-x) AND THE MAXIMUM ACCUMULATED DILATION VELOCITY OVER THE SAMPLES BETWEEN -X TO -X-Y (T-x-y) |
| 3 | MAXIMUM DILATION VELOCITY OVER T-x |
| 4 | MAXIMUM DILATION ACCELERATION OVER T-x |
| 5 | DIFFERENCE BETWEEN MAXIMUM VELOCITY OVER T-x MINUS MEAN VELOCITY OVER T-x-y |
| 6 | DIFFERENCE BETWEEN MAXIMUM VELOCITY OVER T-x AND MAXIMUM VELOCITY OVER T-x-y |
| 7 | DIFFERENCE BETWEEN MAXIMUM PUPIL AREA OVER THE PREVIOUS 0.2S AND THE MEAN PUPIL AREA OVER THE PERIOD FROM 0.2 TO 0.4 SECONDS PRECEDING THE CURRENT SAMPLE |
| 8 | MAXIMUM PUPIL VELOCITY OVER T-x |
| 9 | PRODUCT OF FEATURES 7 (MEASURE OF AREA CHANGE) AND FEATURE 8 (MEASURE OF VELOCITY CHANGE) |
| 10 | MAXIMUM PUPIL DIAMETER OVER T-x |
| 11 | DIFFERENCE OF MAXIMUM DIAMETER OVER T-x MINUS MEAN DIAMETER OVER T-x-y |
| 12 | ABSOLUTE DIFFERENCE BETWEEN MAXIMUM NORMALIZED DIAMETER DEVIATIONS FROM MOVING AVERAGE OVER T-x AND THE MOVING AVERAGE OF PUPIL DIAMETER OVER T-x-y |
| 13 | DIFFERENCE BETWEEN MAXIMUM NORMALIZED DIAMETER DEVIATIONS FROM MOVING AVERAGE OVER T-x AND T-x-y |
| 14 | DIFFERENCE BETWEEN MAXIMUM NORMALIZED VELOCITY OVER T-x AND MOVING AVERAGE OVER T-x-y |
| 15 | DIFFERENCE BETWEEN MAXIMUM NORMALIZED ABSOLUTE VELOCITY OVER THE LAST 4 SAMPLES AND ITS VALUE OVER T-x-y |
| 16 | DIFFERENCE BETWEEN MAXIMUM NORMALIZED VELOCITY T-x AND ITS MOVING AVERAGE |
| 17 | DIFFERENCE BETWEEN THE PERCENTAGE OF SAMPLES IN PERIOD T-x ABOVE THE DIAMETER AT SAMPLE -X AND THE PERCENTAGE OF SAMPLES IN THE PERIOD T-x-y ABOVE THE -X SAMPLE |
| 18 | DIFFERENCE BETWEEN THE PERCENTAGE OF SAMPLES IN PERIOD T-x BELOW THE DIAMETER AT SAMPLE -X AND THE PERCENTAGE OF SAMPLES IN THE PERIOD T-x-y BELOW THE -X SAMPLE |
| 19 | AVERAGE ENERGY OVER T-x CALCULATED AS THE MEAN SQUARE VALUE FOR HISTOGRAM-BASED PROBABILITY DENSITY FUNCTION OF NORMALIZED DIAMETER |
| 20 | POWER RATIO OF THE PEAK SAMPLE IN A WINDOW CENTERED ON SAMPLE -X VERSUS ALL THE SAMPLES IN THE WINDOW |
| 21 | DIFFERENCE BETWEEN CONTOUR ENERGY IN THE PERIOD ENCOMPASSING T-x AND T-x-y |

FIG.5b

FUSION-BASED SPATIO-TEMPORAL FEATURE DETECTION FOR ROBUST CLASSIFICATION OF INSTANTANEOUS CHANGES IN PUPIL RESPONSE AS A CORRELATE OF COGNITIVE RESPONSE

CROSS-REFERENCE TO RELATED APPLICATIONS

This application claims benefit of priority under 35 U.S.C. 120 as a continuation-in-part of co-pending U.S. Utility application Ser. No. 11/965,325 entitled "Coupling Human Neural Response with Computer Pattern Analysis for Single-Event Detection of Significant Brain Responses for Task-Relevant Stimuli" and filed on Dec. 27, 2007, the entire contents of which are incorporated by reference.

BACKGROUND OF THE INVENTION

1. Field of the Invention

This invention relates to the detection of a significant cognitive response to relevant stimuli and more specifically to the detection and classification of instantaneous changes in pupil response as a correlate to cognitive response.

2. Description of the Related Art

A person's cognitive responses may be monitored to study human neurophysiology, perform clinical diagnosis and to detect significant responses to task-relevant or environmental stimuli. In the latter, the detection of such a response may be fed back or used in some manner in conjunction with the task or environment. The detection of a significant cognitive response does not classify the stimulus but generates a cue that the operator's neurophysiology has responded in a significant way. Various techniques for monitoring cognitive responses include electroencephalography (EEG), pupil dilation and function near IR spectroscopy (FNIRS), each of which has been correlated to changes in neurophysiology.

Pupil response provides a direct window that reveals sympathetic and parasympathetic pathways of the autonomic division of the peripheral nervous system. Task-evoked pupil dilations are known to be a function of the cognitive workload and attention required to perform the task. It has long been known that the pupil dilates in response to emotion evoking stimuli. Thus, cognitive task related pupillary response provides a modality that can be used to detect significant brain responses to task-relevant stimulus. Measurements of pupil dilation include averaging procedures, differencing of adjacent observations and smoothing techniques.

U.S. Pat. No. 6,090,051 suggests subjecting a subject's pupillary response to wavelet analysis to identify any dilation reflex of the subject's pupil during performance of a task. A pupillary response value is assigned to the result of the wavelet analysis as a measure of the cognitive activity. Wavelet analysis employs a mother wavelet selected from the Daubechies family of wavelets, Symlet wavelets, Coiflet wavelets, Morlet wavelets, the Battle-Lemarie family of wavelets and the Chui-Wang family of wavelets. The mother wavelet is applied iteratively to decompose the pupillary response into orthogonal transformations of the response at different frequencies or scale, each of which can be analyzed and interpreted.

The wavelet is a form of "matched filter" designed to detect specific high-frequency patterns of the signal under specific environmental conditions e.g. a subject performing specific tasks in a controlled environment. As such the wavelet is not robust to variations in stimuli or changes in environmental conditions e.g. noise. De-noising techniques do not fully address this issue. Furthermore, wavelet analysis makes a commitment to the high-frequency properties of a signal and lacks an ability to capture other qualitatively important measures of the pupil dilation behavior. Wavelet analysis is a complex non-linear calculation that does not lend itself to simple, fast hardware implementations.

SUMMARY OF THE INVENTION

The present invention provides a computationally efficient and robust approach for monitoring the instantaneous pupil response as a correlate to significant cognitive response to relevant stimuli.

In an embodiment, a sensor measures the pupillary response of a subject subjected to stimuli in an environment. A pre-processor derives data samples d(n) of the pupil diameter (area), v(n) of pupil velocity and a(n) of pupil acceleration from the pupillary response and segments the data samples into a sequence of time-shifted windows, typically overlapping and perhaps sample-by-sample. Each window includes a response period and a baseline period. A feature extractor extracts a plurality of spatio-temporal pupil features from the data samples d(n), v(n) and a(n) from the response and baseline periods in each window. Absolute features are extracted from samples in only the response period while comparative features are extracted from samples in both the response and baseline periods.

A classifier, preferably linear, trained to detect patterns of the extracted spatio-temporal pupil features for relevant stimuli generates an output indicative of the occurrence of absence of a significant cognitive response in the subject to a relevant stimulus. The output may be a likelihood (continuous 0 to 1) or decision (binary 0 or 1) and is suitably generated in real-time. This output may be fed back as a feature for the next window. A post-processor may be used to synthesize the one or more temporal outputs indicative of the occurrence of a significant cognitive response to a particular relevant stimulus to reinforce or reject the decision and/or to refine the time-stamp of the detected stimulus.

Feature level fusion of absolute and comparative spatio-temporal pupil features derived from the diameter, velocity and acceleration samples provides both a simple and robust classifier. The classifier may be implemented as a linear classifier that lends itself to simple hardware designs. The extracted features and classification are robust to changes in the background environment, relevant stimuli and cognitive responses.

These and other features and advantages of the invention will be apparent to those skilled in the art from the following detailed description of preferred embodiments, taken together with the accompanying drawings, in which:

BRIEF DESCRIPTION OF THE DRAWINGS

FIG. 2 is a diagram illustrating the baseline and response periods with respect to the occurrence of a stimulus;

FIGS. 3a and 3b illustrate different windowing approaches to extract features from the baseline and response periods to investigate a sample;

FIGS. 5a and 5b are tables of the same absolute and comparative spatio-temporal pupil features for the different windowing approaches;

DETAILED DESCRIPTION OF THE INVENTION

The present invention provides a computationally efficient and robust approach for monitoring the instantaneous pupil response as a correlate to significant cognitive response to relevant stimuli.

In an embodiment, a sensor measures the pupillary response of a subject subjected to stimuli in an environment. A pre-processor derives data samples d(n) of the pupil diameter (area), v(n) of pupil velocity and a(n) of pupil acceleration from the pupillary response and segments the data samples into a sequence of time-shifted windows, typically overlapping and perhaps sample-by-sample. Each window includes a response period and a baseline period. A feature extractor extracts a plurality of spatio-temporal pupil features from the data samples d(n), v(n) and a(n) from the response and baseline periods in each window. Absolute features are extracted from samples in only the response period while comparative features are extracted from samples in both the response and baseline periods.

A classifier, preferably linear, trained to detect patterns of the extracted spatio-temporal pupil features for relevant stimuli generates an output indicative of the occurrence of absence of a significant cognitive response in the subject to a relevant stimulus. The output may be a likelihood (continuous 0 to 1) or decision (binary 0 or 1) and is suitably generated in real-time. The likelihood is the probability that a significant response has occurred in response to a relevant stimulus. This output may be fed back as a feature for the next window. A post-processor may be used to synthesize the one or more temporal outputs indicative of the occurrence of a significant cognitive response to a particular relevant stimulus to reinforce or reject the decision and/or to refine the time-stamp of the detected stimulus.

Feature level fusion of absolute and comparative spatio-temporal pupil features derived from the diameter, velocity and acceleration samples provides both a simple and robust classifier. The classifier may be implemented as a linear classifier that lends itself to simple hardware designs. The extracted features and classification are robust to changes in the background environment, relevant stimuli and cognitive responses.

Figure 1A:
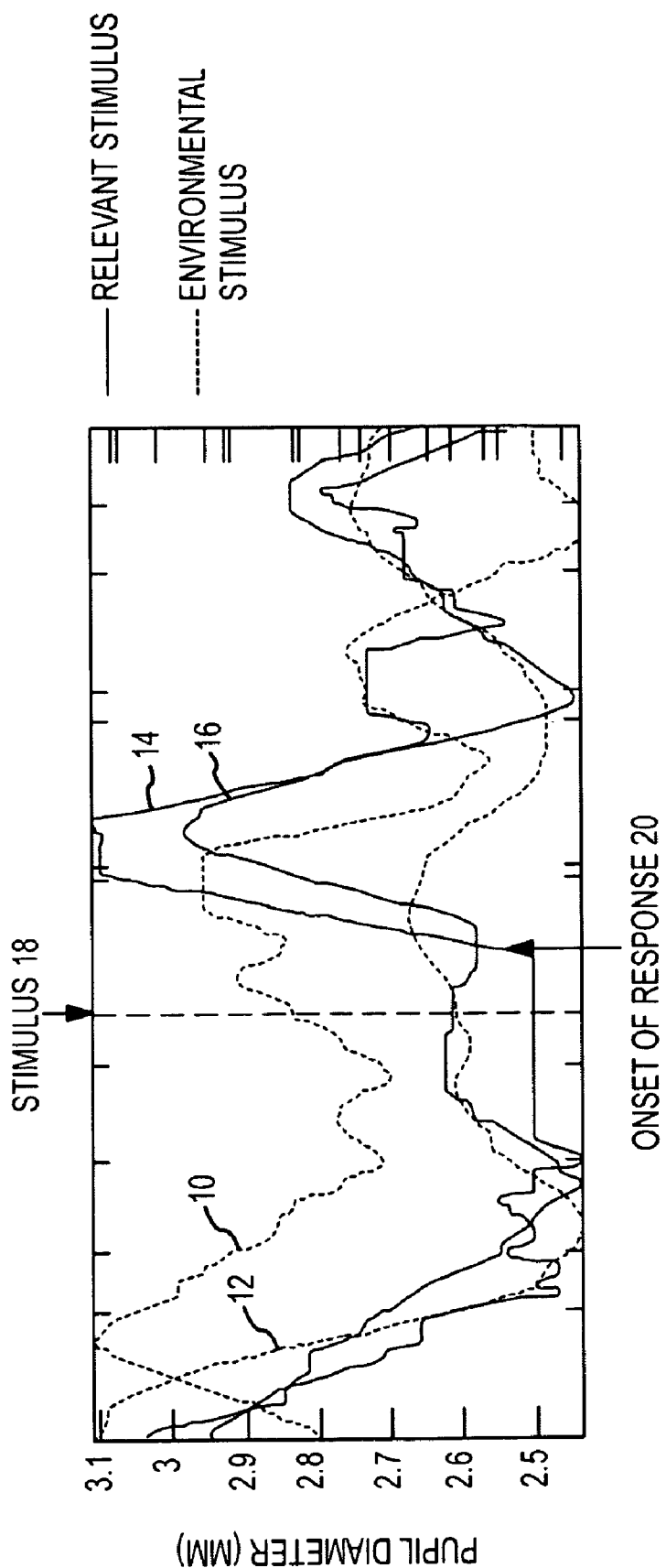
FIGS. 1a and 1b are plots of single and trial-averaged pupil response to relevant and non-relevant stimuli.

To better understand the fusion-based feature extraction and classification system for detecting pupillary responses as a correlate for significant brain response, we will first consider representative single-trial temporal pupillary responses 10 and 12 to non-relevant environmental stimuli and responses 14 and 16 to relevant stimuli as shown in FIG. 1a. In general, a subject's pupillary response is fairly random, increasing and decreasing with changing environmental stimuli. However, the presentation of a relevant visual stimulus 18, one that evokes a significant cognitive response, induces a rather dramatic pupillary response e.g. a large and rapid increase in diameter, as shown in responses 14 and 16. In a typical human, the onset 20 of the pupillary response has a latency of approximately 200 ms. The pupillary response itself has a duration of approximately 800 ms. The latency and duration will vary with individual subjects or classes of subject (e.g. age).

A relevant stimulus may consist of a point of reference on a visual display, a unit of visual information which is intended to invoke some response in a subject viewing the display, any visual indicator which is intended to attract the attention of the subject, or any event intended to invoke cognitive activity. The presentation of stimuli may be controlled such as in an RSVP system or occur randomly in more robust environments. Detection of pupillary response as a correlate to cognitive response is particularly difficult in a robust environment in which the baseline conditions and relevant stimuli are different and changing compared to the training environment.

Figure 1B:
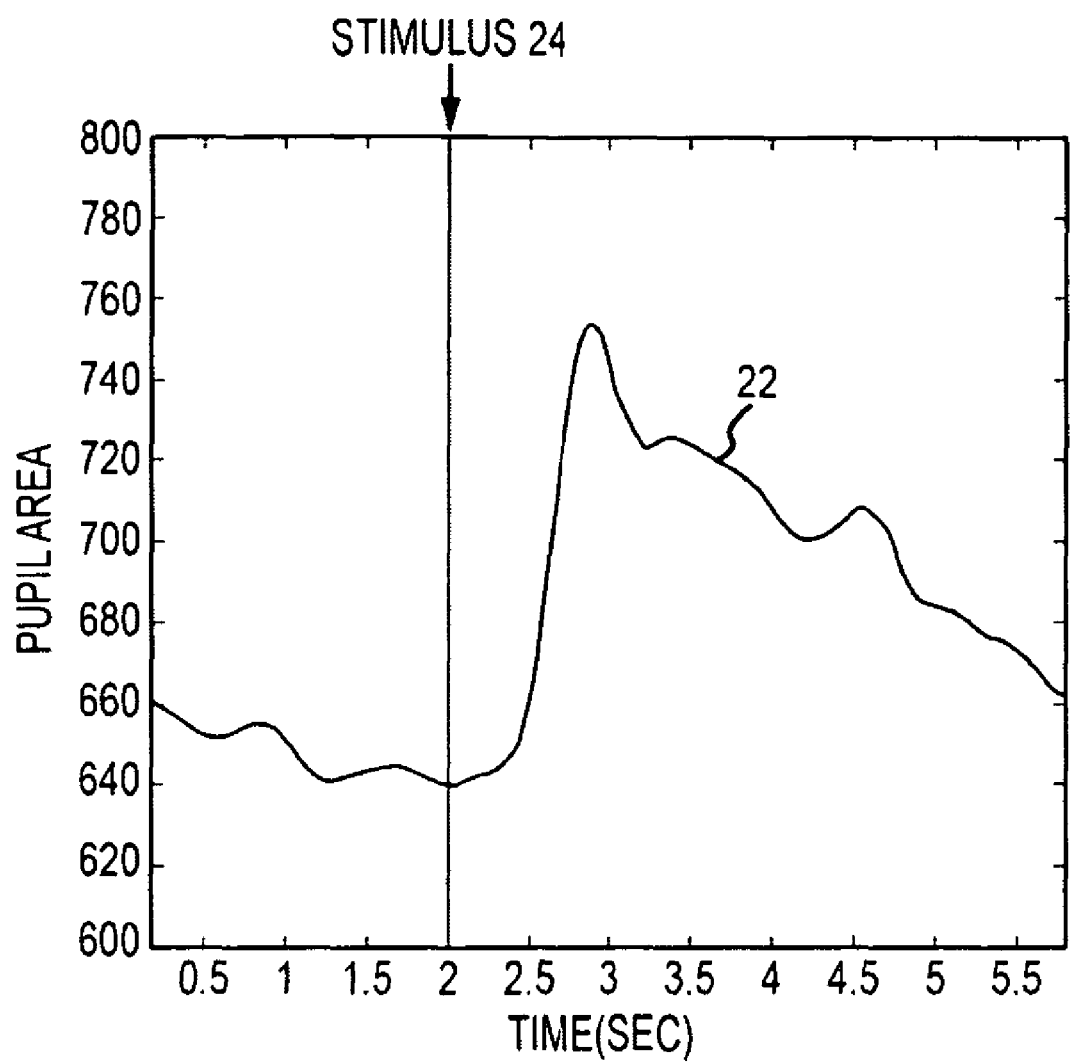

The difference in pupillary response to a relevant stimulus as opposed to baseline environmental conditions may be fairly pronounced. This is clearly shown in a trial-averaged pupillary response 22 to a relevant stimulus 24 as shown in FIG. 1b. The large and rapid increase in pupil diameter is preceded by a smaller more stable diameter. However, in most applications trial-averaging is not practicable. Instead, detection and classification must be made based on noisy single-trial responses like those shown in FIG. 1a.

As shown in FIG. 2, the temporal pupillary response to a relevant stimulus 30 can be segmented into components: a pre-stimulus period 32, a latency period 34 and a critical response period 36. To a good approximation, the pre-stimulus period ranges from 300 ms to 1 second prior to the stimulus, the latency period is approximately 200 ms and the critical response period is approximately 800 ms. To extract simple, useful and robust spatio-temporal features from the pupillary response we chose to simplify to a "response period" 40 and a "baseline period" 42. Depending on how one chooses to compute features and implement the classifier, the latency period 32 may be included in either the response period 40 or the baseline period 42.

Pattern recognition is often based on derived features from the original signal rather than based on the original signal itself. In the pupillary response, the original signal has only a single channel. To maximize the information content of the pupil signal, we identified a set of spatio-temporal features related to pupillary response that can be derived from the original pupil diameter data d(n). The plurality of features for any particular classifier is selected during training from the rich set of features. These features can be essentially labeled as either "absolute" or "comparative" pupil features, each including diameter (area), velocity and area features.

Absolute pupil features are computed from data samples d(n) in only response period 40. These features measure the "absolute" pupil response to the relevant stimulus. Comparative features are computed from data samples d(n) in both the response period 40 and baseline period 42. These features compare the pupil response to the relevant stimulus to the baseline response.

The pupillary response is typically measured continuously and sampled to generate a time-sequence of data samples d(n) representative of the diameter or area of the pupil. These samples are typically segmented into a sequence of time-shifted windows, typically overlapping and perhaps shifted by a single sample. As long as the time windows include both a response period preceded by a baseline period, the windows can be constructed to position the 'investigation sample' in different locations, to assume an ideal location of a relevant stimulus if one exists and to extract the features accordingly in many different ways. The classifier generates an output O(n) that is paired to a particular data sample d(n) i.e. the "investigation sample". Two different approaches are illustrated in FIGS. 3a and 3b. Although the nomenclature and presentation are different the actual extraction of features, classification and results will be very similar.

A first approach, "response onset", defines each window 50 with the investigation sample 52 positioned at a known position within the window e.g. the center of the window as shown here, one-third of the way into the window, etc. The window is ideally constructed for the investigation sample 52 to correspond to the onset of the pupillary response to a relevant stimulus. The X leading samples in front of the investigation sample define the response period 54 and the Y lagging samples in back of the investigation sample define the baseline period 56. The stimulus 58 offset by the latency of the pupil response will typically lie within the baseline period 56. The absolute and/or comparative features selected for a given application are extracted from the window and presented to the classifier. The classifier generates an output, either a likelihood output O(n) (0 to 1) or a decision output (0 or 1) that is paired with investigation sample d(n) from the center of the window. Assuming a relevant stimulus exists, as the classifier processes the sequence of time-shifted windows the classifier output will start to indicate the presence of a relevant stimuli once a portion of the response is captured in the window. As the window shifts in time and becomes better aligned with the pupillary response the classifier output will be stronger e.g. a likelihood output will increase towards 1 and the decision output will achieve increased classification confidence. The temporal sequence of classifier outputs O(n) can be post-processed to reinforce or reject the output and, if reinforced, to refine the time-stamp on the pupillary response, hence the stimulus. Accuracies to within a single sample are obtainable.

A second approach, "current sample", defines each window 60 with the investigation sample 62 positioned at the leading edge of the window. Therefore, the classifier output indicates whether the current sample is associated with a significant cognitive response triggered by a relevant stimulus presented at the Xth sample prior to the current sample. The window is ideally constructed for the investigation sample 62 to correspond to the peak of the pupillary response to a relevant stimulus. The preceding X samples between the investigation sample and the assumed position of any stimulus 64 define the response period 66 and the Y samples preceding the stimulus define the baseline period 68. In this construct, the latency period is part of the response period 66. Although the features are defined with different nomenclature, they are extracted from the sequence of time-shifted windows in the same manner and presented to the classifier that generates a time sequence of outputs O(n) that are paired with the investigation sample 62. As the investigation sample starts to see more evidence of a pupillary response, the strength of the classifier output will increase as before. If a sufficient response is measured, the response is attributed to a stimulus present at time -X from the current sample. Again, this decision can be reinforced or rejected, and if reinforced, refined in time using temporal processing.

The rich set of spatio-temporal features can be further expanded to include diameter (area), velocity and acceleration features for each of the absolute and comparative pupil feature classes. In a typical embodiment, data samples v(n) for the instantaneous velocity and a(n) for the instantaneous acceleration are computed for each sample in the window. For example, v(n) may be computed as d(n)-d(n-1)/T or d(n+1)-d(n-1)/2T and a(n) may be computed as v(n)-v(n-1)/T or v(n+1)-v(n-1)/2T.

Figure 4A:
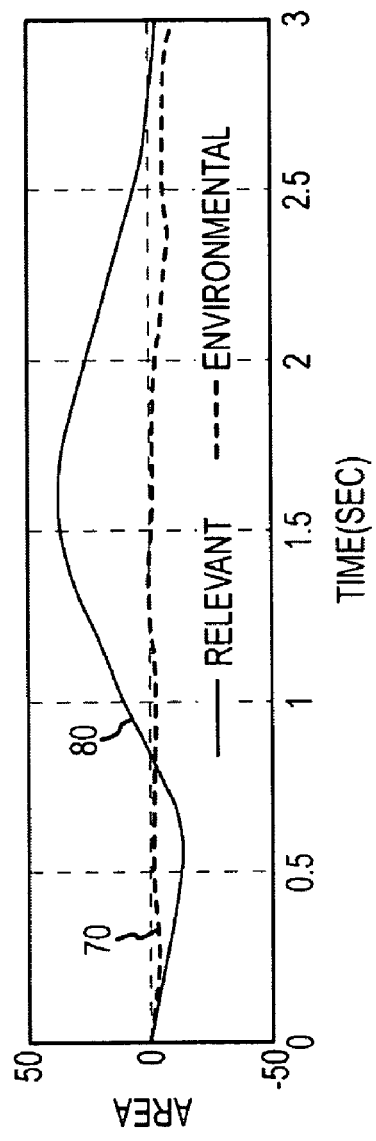
FIGS. 4a through 4c are plots of pupil area, velocity and acceleration response to a relevant stimulus.
Figure 4B:
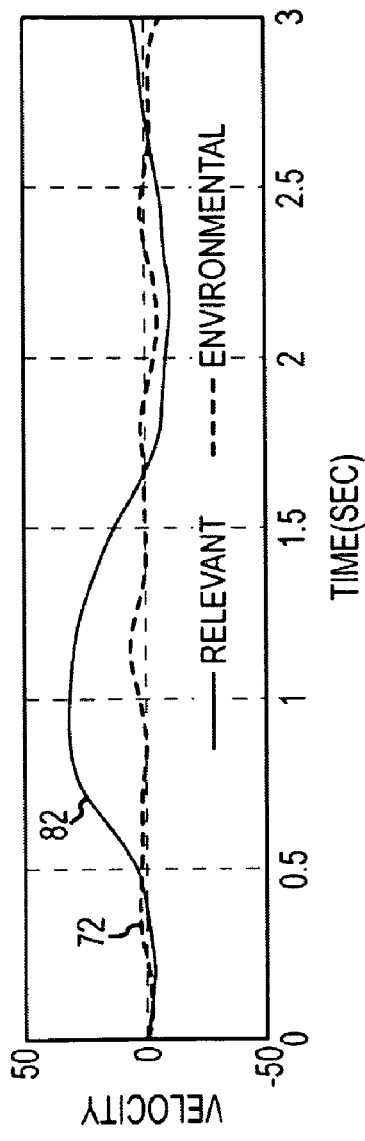
Figure 4C:
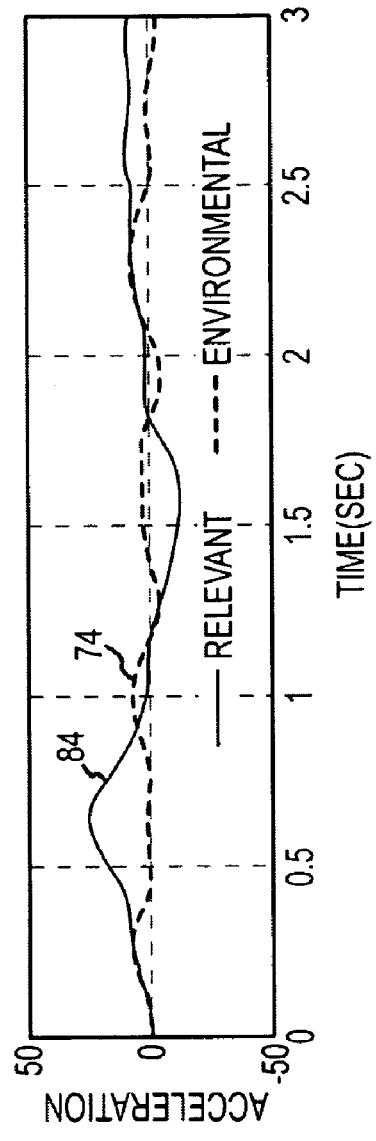

FIGS. 4a-4c provide a comparison of time-average pupil area 70, velocity 72 and acceleration 74 features for environmental stimulus and time-average pupil area 80, velocity 82 and acceleration 84 features for a relevant stimulus presented at t=0. The velocity feature shows earlier differentiation between relevant and environmental stimuli compared to the area feature. The acceleration feature shows even earlier differentiation. The selection of the best area/velocity/acceleration features for absolute and comparative features and the fusion of those features for presentation to the classifier improve classifier performance and robustness.

There can be many variants of the area/velocity/acceleration features for the absolute and comparative features that can be constructed to form a training set for selecting a subset of a plurality of those features for any particular classifier. Tables 90 and 92 of representative training sets for the "response onset" and "current sample" constructs are illustrated in FIGS. 5a and 5b.

As shown in FIGS. 5a and 5b, the training set includes twenty-two spatio-temporal features. Of these six features (F1, F3, F4, F8, F10 and F20) are absolute features and sixteen features (F2, F5-F7, F9, F11-F19, F21 and F22) are comparative features. Of the six absolute features F10 is a diameter feature, three features (F1, F3 and F8) are velocity features, F4 is an acceleration feature and F20 is an energy feature. Of the sixteen comparative features, seven are diameter/area features (F7, F11, F12, F13, F14, F18, F19), six are velocity features (F2, F5, F6, F15, F16, F17) and three are other features (F9, F21 and F22). Many of these features are highly correlated. The training process down selects the subset of features that provides the best performance for a given application. Depending on the number of features selected for the implemented classifier, a typical set will include both absolute and comparative features and a mix of diameter/area, velocity and acceleration features to maximize class separability over the training data.

Figure 6:
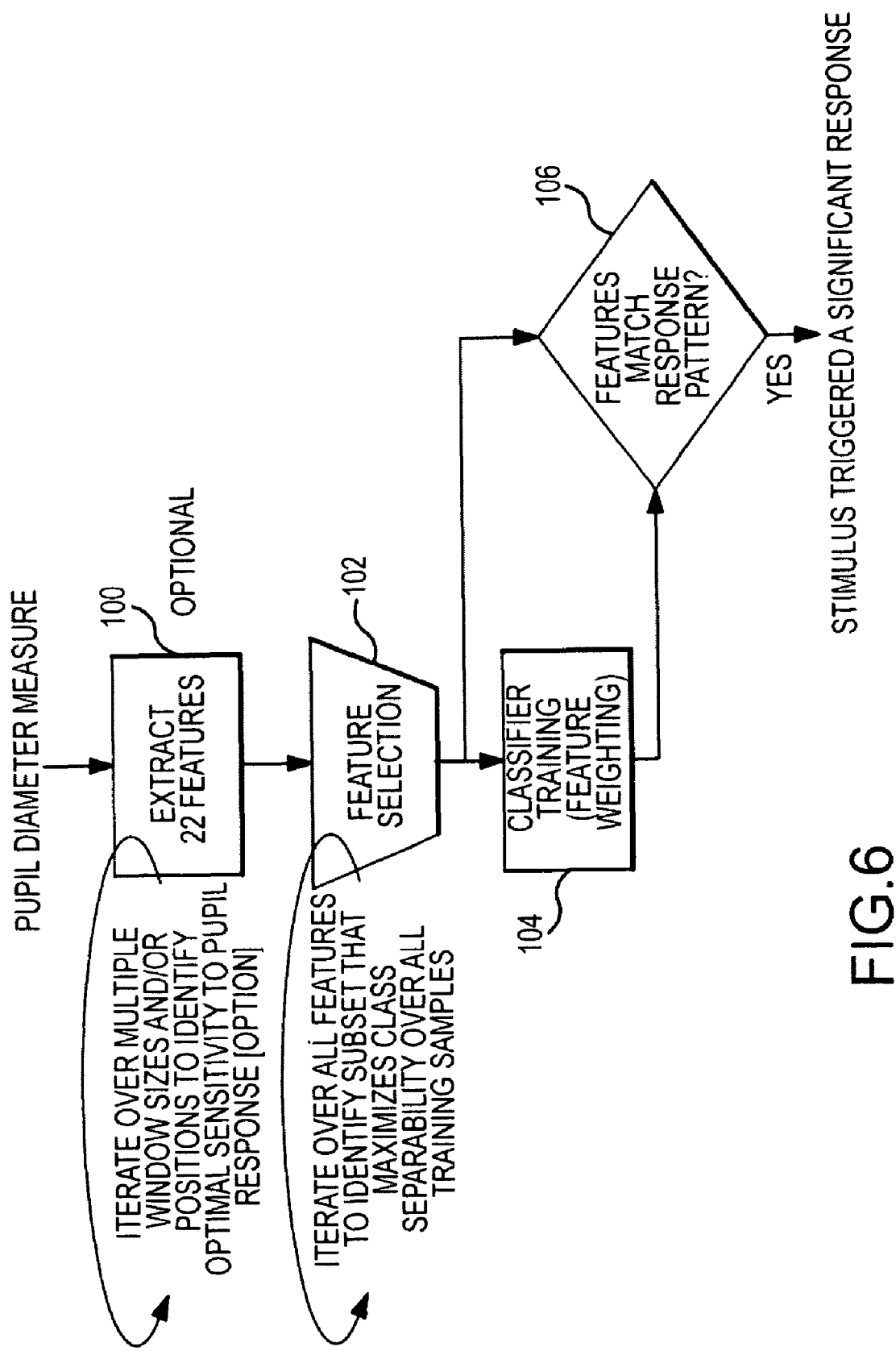
FIG. 6 is a flow diagram for configuring and training a classifier to fuse a subset of pupil features and to detect patterns of those features.

A flow diagram of a representative training process for selecting a subset of features, possibly optimizing the window size, in particular the response period, and weighting the selected features is illustrated in FIG. 6. During training the presentation of relevant stimulus and baseline environmental stimuli is known. To extract pupil dilation features, a time window is set around each stimulus (relevant or baseline) event in accordance with the selected windowing approach e.g. "response onset" or "current sample" and the pupil diameter d(n), pupil diameter changing velocity v(n), changing acceleration a(n) and pupil area ar(n) are derived for all time samples inside the time window. Using the tables shown in FIGS. 5a and 5b=a total of 22 features are extracted from the raw pupil dilation data (step 100). Optionally, the feature extraction process may be iterated over multiple window sizes e.g. multiple "response period" sizes to identify optimal sensitivity to pupil response for an individual or class of subjects.

For a given application e.g. subjects, relevant stimuli, baseline environmental stimuli, etc. a feature selection process (step 102) is performed to select a subset of d features, 1<d<22, that are the most appropriate. In general, the process selects the features that maximize class separability (relevant vs. non-relevant stimulus) over all training data. The process typically either specifies the number of features in the subset and then picks the best features or specifies a performance criteria and picks the best and fewest features required to satisfy the criteria. The benefits of the feature selection procedure are two-fold: it could reduce the computational cost of classification by reducing the number of features that need to be calculated, and it could improve classification accuracy by fitting a simpler model based on a finite number of training samples.

One process of feature selection is sequential forward floating selection (SFFS). Given the 22 candidate features described in previous section, a subset of d features, d<22, is selected that performs the best under the selected classifier (e.g. a linear discriminator analysis (LDA) classifier). SFFS starts from an empty feature subset and sequentially selects the one most significant feature at a time and adds it to the feature subset to maximize the cost function J until a predefined feature number is obtained (or a predefined cost function obtained). The classification error over a training set is used as the cost function J. Sequential backward selection (SBS) is another selection process that's starts from a subset with all d features and selectively deletes one least significant feature at a time until a predefined feature number is obtained. Both SFS and SBS methods have the so-called nesting problem: once a feature is added/deleted, it cannot be deleted/added anymore. The SFFS method avoids the nesting problem by correcting earlier 'mistakes' by backtracking: first enlarge the feature subset by adding l most significant features using SFFS, then delete r least significant features using SBS. The l and r are determined dynamically ("floating") so as to approximate the optimal solution.

Once the subset of features has been selected for a specified classifier, the classifier weights must be trained (step 104) until the presented features from the training data match the response patterns (step 106). By linearly combining multiple pupillary-based features, an aggregate representation of the data can be obtained. Let d be the observed vector of pupillary response based selected features, an optimal projection weighting vector $w_{pupil}$ can be derived based on a training set and so that a one-dimensional projection $y_{pupil}$ can be derived:

$$y_{pupil}(t) = w_{pupil}^T d = \text{SUM}(w_{pupili} d_i) \text{ for } I=1 \text{ to } D$$

where D is the number of pupillary response based features selected using the SFFS method. The projection $y_{pupil}(t)$ can be assumed to follow some distributions of the exponential family and is regarded as a better estimate of neurophysiologic activity than any individual pupillary response feature.

Receiver operating characteristic (ROC) curves can be obtained using p(H1|d) and comparing it with a threshold $\theta_{pupil}$. $\theta_{pupil}$ can take on values within the range [0, 1]. The decision rule can be $p(H1|x) \geq \theta_{pupil}$, $u_{pupil}=1$ and $p(H1|x) < \theta_{pupil}$, $u_{pupil}=0$ or vice versa where $u_{pupil}=1$ represents a classifier's decision to declare a relevant detection and $u_{pupil}=0$ represents a classifier's decision to declare a non-relevant (environmental) detection.

Figure 7:
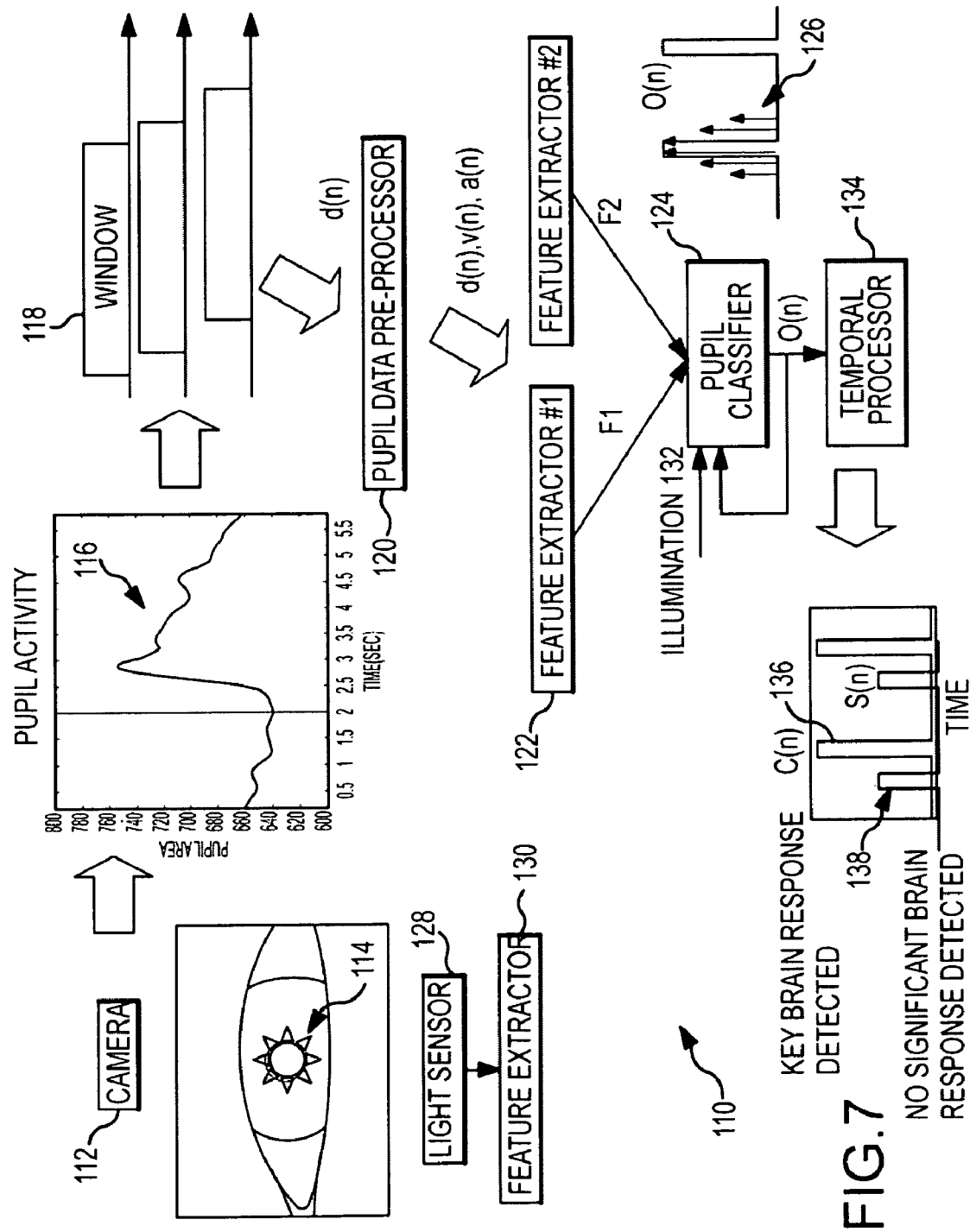
FIG. 7 is a diagram of a fusion-based spatio-temporal classifier.
Figure 8A:
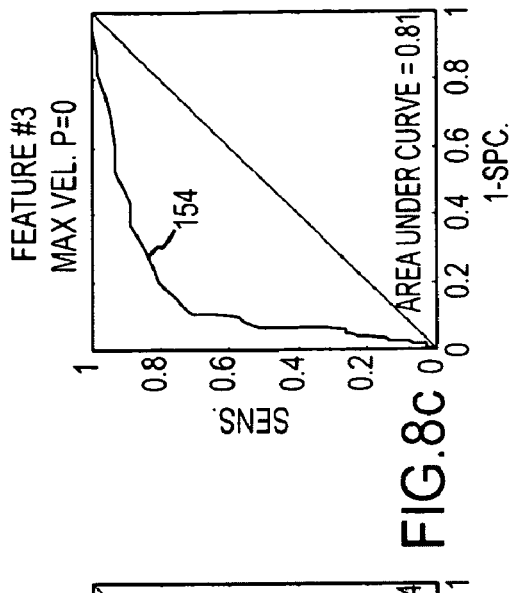
FIGS. 8a through 8f are plots of the individual receiver operating curves (ROCs) for six different area, velocity and acceleration features.
Figure 8B:
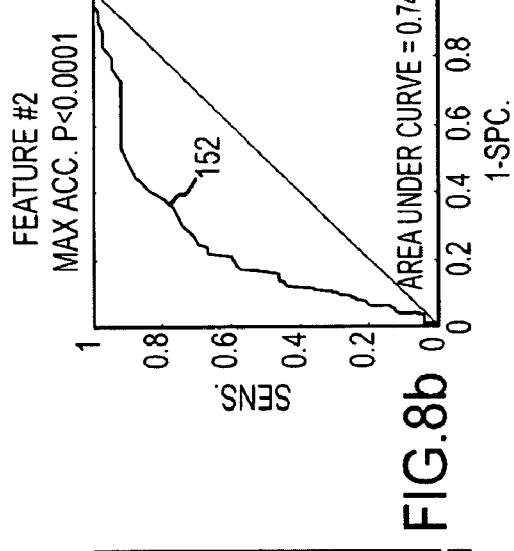
Figure 8C:
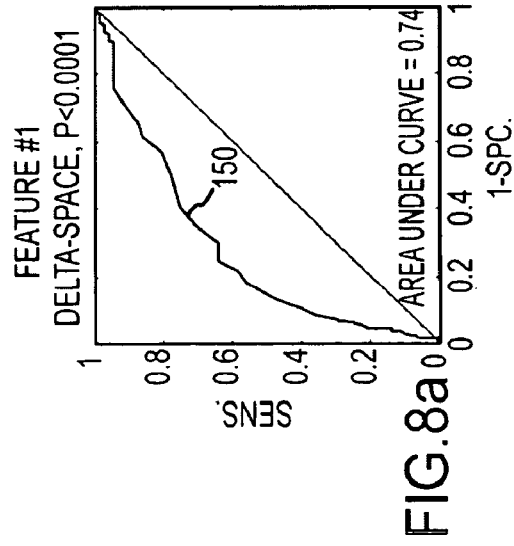
Figure 8D:
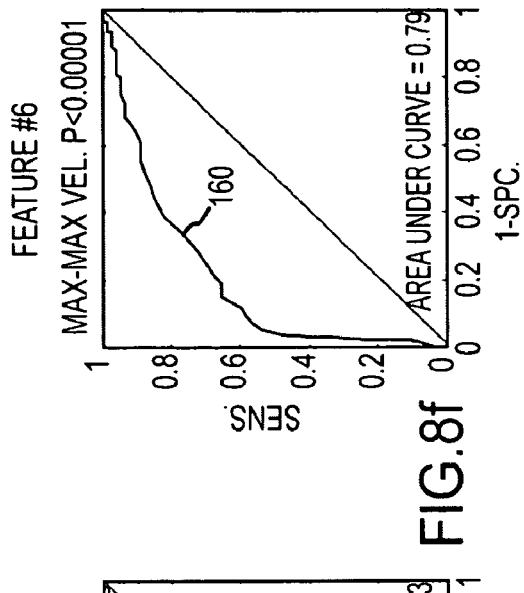
Figure 8E:
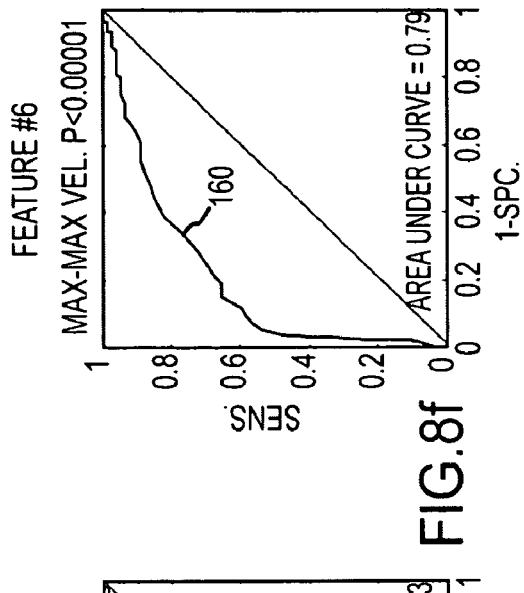
Figure 8F:
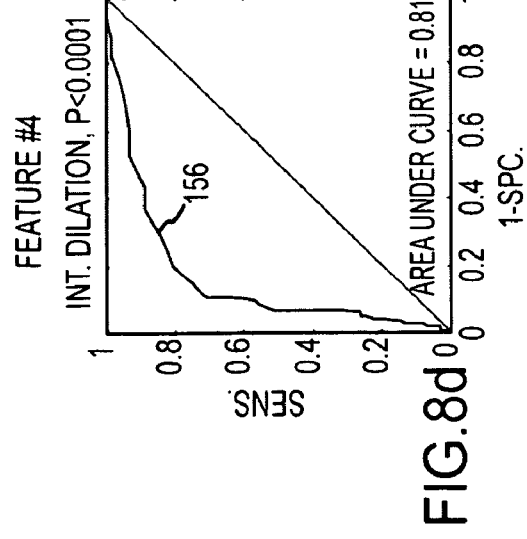

A system 110 for using the selected subset of features and trained classifier to detect pupillary response as a correlate to cognitive response to relevant stimuli is shown in FIG. 7. A camera 112 such as an EyeLink 1000 video based eye tracking device is trained on the subject's pupil 114 to monitor pupil activity 116 e.g. size, continuously over time. The EyeLink1000 measures pupil area data ar(n) at 1000 Hz sampling rate. Pupil diameter data d(n) (in millimeter units) are generated using pupil area data ar(n) in pixels (the conversion relationship is 13.5 pixels per square millimeter). The pupil diameter data d(n) is segmented into a sequence of time-shifted windows 118, typically overlapping. The windows may shift by only a single sample.

The pupil size data can be corrupted by eye blinks. The pupil size monitoring device actually has an eye blink detection mechanism implemented. A pupil data pre-processor 120 removes all corrupted pupil size data associated with eye blink regions and interpolates the data to fill in the missing data segments created by eye blinks. A moving averaging filter is then used to smooth the pupil area data to improve the signal-to-noise ratio. The pre-processor also suitably computes velocity v(n) and acceleration d(n) values for each sample in the response and baseline periods of the window as needed to support extraction of features in the selected subset.

Feature Extractors 122 process the appropriate data samples d(n), v(n) and a(n) in the response and/or baseline periods to compute their respective features F1, F2, F3 etc. from the selected subset. For each window, the extracted pupil features are presented to the classifier 124 trained to detect patterns of the extracted spatio-temporal pupil features for relevant stimuli and generate an output O(n) indicative of the occurrence or absence of a significant cognitive response in the subject to a relevant stimulus. The classifier may be a feature-based classifier that generates a likelihood output O(n) (0 to 1) or a decision-based classifier that generates a binary output (0 or 1) that is paired with investigation sample d(n) from the window. The classifier is suitably a linear classifier trained to detect patterns of linearly weighted combinations of the extracted spatio-temporal pupil features.

Assuming a relevant stimulus exists, as the classifier processes the sequence of time-shifted windows the classifier output O(n) 126 will start to indicate the presence of a relevant stimuli once a portion of the response is captured in the window. As the window shifts in time and becomes better aligned with the pupillary response the classifier output will be stronger e.g. a likelihood output will increase towards 1 and the decision output will achieve increased classification confidence. Consequently, the output O(n) may be fed back as a feature to classify the next window.

Changing light conditions may cause the subject's pupil to dilate as if in response to a relevant stimulus producing a false positive. A light sensor 128 may be used to measure light conditions. A feature extractor 130 extracts a light feature 132 indicative of illumination changes and presents the light feature to the classifier to discount puppilary responses due to illumination changes. The method can apply one of two approaches. The first approach is to deconvolve a light-related reflex response from the ongoing pupillary response signal. The second approach is to eliminate from analysis, any such periods that are associated with significant reduction in illumination of the environment.

A temporal post-processor 134 may be used to process the temporal sequence of classifier outputs O(n) to reinforce or reject the output and, if reinforced, to refine the time-stamp on the pupillary response, hence the stimulus. The time sequence of feature-level outputs O(n) may produce decision-level classifier outputs C(n) 136 and stimulus outputs S(n) 138. The stimulus S(n) is offset ahead of the output O(n) by a fixed amount to compensate for the latency of the pupil response and the position of the investigative sample. Accuracies to within a single sample are obtainable.

Figure 9:
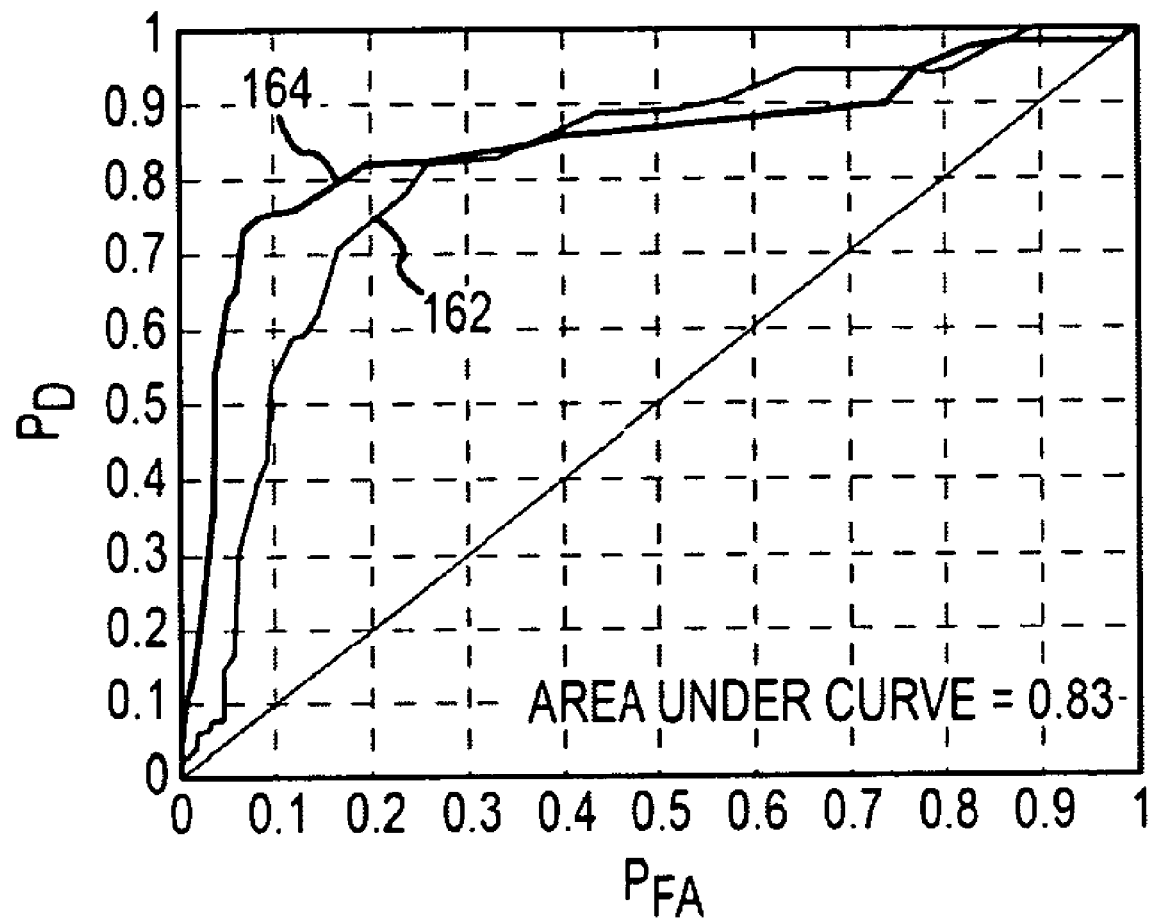
FIG. 9 is a plot of ROCs for an optimal single feature and an optimal pair of fused features.

Receiver operating curves (ROCs) 150, 152, 154, 156, 158 and 160 for features F1 through F6 respectively are shown in FIGS. 8a through 8f. The ROC plots the probability of a correct detection against the probability of a false alarm. FIG. 9 is a plot of the ROC 162 for the best single feature (F5) and the ROC 164 for the best pair of fused features (F2 and F7). As illustrated, the fusion of just two complementary features improved performance markedly.

While several illustrative embodiments of the invention have been shown and described, numerous variations and alternate embodiments will occur to those skilled in the art. Such variations and alternate embodiments are contemplated, and can be made without departing from the spirit and scope of the invention as defined in the appended claims.

We claim:

1. A method for detecting relevant stimuli using pupillary response as a correlate to cognitive response, comprising:

providing a classifier, said classifier trained to detect patterns of spatio-temporal pupil features and generate an output indicative of the occurrence or absence of a relevant stimulus that evokes both a cognitive response and a pupillary response in a subject;

using a sensor to measure the pupillary response of a subject subjected to stimuli in an environment, wherein the occurrence of a relevant stimulus is initially unknown to the classifier;

deriving data samples d(n) of the pupil diameter from the pupillary response;

segmenting the data samples d(n) into a sequence of time-shifted windows, each window including a response period and a baseline period;

extracting a plurality of spatio-temporal pupil features from the data samples d(n) in said response and baseline periods in each said window; and for each said window, presenting the extracted pupil features to the classifier to generate an output indicative of the occurrence or absence of a relevant stimulus.

2. The method of claim 1, wherein said plurality of pupil features includes at least one comparative pupil feature extracted from samples d(n) in both the response and baseline periods.

3. The method of claim 2, wherein said at least one comparative pupil feature is a difference between a first diameter, velocity or acceleration feature computed from samples d(n) in the response period and a respective second diameter, velocity or acceleration feature computed from samples d(n) in the baseline period.

4. The method of claim 2, wherein said plurality of pupil features includes at least one absolute pupil feature extracted from samples d(n) in only the response period.

5. The method of claim 4, wherein at least one of the absolute pupil features is a diameter, velocity or acceleration feature.

6. The method of claim 4, wherein at least one of the absolute or pupil features is a velocity or acceleration feature.

7. The method of claim 1, further comprising deriving data samples v(n) of the velocity and a(n) of the acceleration, said pupil features including a diameter, a velocity and an acceleration feature computed from the d(n), v(n) and a(n) samples in the response and baseline periods.

8. The method of claim 1, further comprising synthesizing the one or more temporal outputs indicative of the occurrence of a significant cognitive response to a particular relevant stimulus to reinforce or reject the output and, if reinforced, to resolve the time-stamp of the stimulus.

9. The method of claim 1, wherein the output is provided as a feature to the classifier for the next time-shifted window.

10. The method of claim 1, further comprising measuring light conditions, extracting a light feature indicative of illumination changes and inputting the light feature to the classifier to discount pupillary responses due to illumination changes.

11. The method of claim 1, wherein the output is paired with a sample of interest d(n) at a specified position within the window, said response period being the X leading samples d(n) in front of the specified position and said baseline period being the Y lagging samples behind the specified position.

12. The method of claim 1, wherein the output is paired with a sample of interest d(n) at the leading edge of the window, said response period being the immediately preceding X samples d(n) and said baseline period being the Y samples preceding the response period.

13. The method of claim 1, wherein the classifier is a linear classifier trained to detect patterns of linearly weighted combinations of said extracted spatio-temporal pupil features.

14. The method of claim 1, further comprising:
providing a training set of spatio-temporal pupil features including absolute diameter, velocity and acceleration features extracted from data samples d(n) in only the response period and comparative diameter, velocity and acceleration features from data samples d(n) in both the response and baseline periods;

selecting the plurality of spatio-temporal pupil features from the training set that separate relevant stimuli from non-relevant stimuli; and training the classifier to detect patterns of the selected plurality of spatio-temporal pupil features.

15. A method for detecting relevant stimuli using pupillary response as a correlate to cognitive response, comprising:
providing a classifier, said classifier trained to detect patterns of pupil features and generate an output indicative of the occurrence or absence of a relevant stimulus that evokes both a cognitive response and a pupillary response in a subject;

using a sensor to measure the pupillary response of a subject subjected to stimuli in an environment, wherein the occurrence of a relevant stimulus is initially unknown to the classifier;

extracting a plurality of pupil features from the measured pupillary response; and presenting the extracted pupil features to the classifier to generate an output indicative of the occurrence or absence of a relevant stimulus.

16. The method of claim 15, wherein the cognitive response is indicative of conscious intellectual activity.

* * * * *